(12) United States Patent
Miller

(10) Patent No.: US 6,608,212 B1
(45) Date of Patent: Aug. 19, 2003

(54) PROCESS FOR PREPARING VINYLAROMATIC COMPOUNDS

(75) Inventor: Joseph Miller, Greenville, NC (US)

(73) Assignees: Pfizer, Inc., New York, NY (US); DSM NV, Heerlen (NL)

(*) Notice: Subject to any disclaimer, the term of this patent is extended or adjusted under 35 U.S.C. 154(b) by 0 days.

(21) Appl. No.: 10/171,419

(22) Filed: Jun. 4, 2002

(51) Int. Cl.$^7$ .................. C07D 207/04; C07C 2/00; C07F 9/09

(52) U.S. Cl. .............. 548/575; 585/427; 568/630; 568/631; 568/633; 558/132

(58) Field of Search .................. 585/422, 425, 585/427, 502, 531; 558/70, 89, 132, 90; 568/579, 626, 630, 631, 633; 548/400, 570, 574, 575

(56) References Cited

U.S. PATENT DOCUMENTS

| | | | | |
|---|---|---|---|---|
| 4,581,380 A | * | 4/1986 | Shroot et al. | 514/732 |
| 5,116,830 A | * | 5/1992 | Tanabe et al. | 514/182 |
| 5,552,412 A | * | 9/1996 | Cameron et al. | 514/317 |
| 5,602,228 A | * | 2/1997 | Wang et al. | 528/397 |
| 5,792,762 A | * | 8/1998 | Bryant et al. | 514/212.01 |
| 6,045,991 A | * | 4/2000 | Akhavan-Tafti | 435/4 |
| 6,103,919 A | * | 8/2000 | Schiraldi et al. | 556/136 |
| 6,271,411 B1 | * | 8/2001 | Nifant'ev et al. | 560/102 |

OTHER PUBLICATIONS

CA:123:279492 abs of Journal of Organic Chem by Kutateladze et al 60(21) pp 6930–6 1995.*
CA:137:185293 abs of Tetrahedron Letters by Nifant'ev et al 43(17) pp 3213–3215 2002.*
CA:111:78367 abs of JP01022890 Jan. 1989.*
CA:107:134384 abs of Journal of Organic Chemistry by Calogeropoulou et al 52(19) pp 4185–4190 1987.*
CA:96:181357 abs of Polish Journal of Chemistry by Zwierzak et al 55(3) pp 631–642 1981.*
CA:113:23322 abs of Archiv der Pharmazie by Schneider et al 323(1) pp 17–21 1990.*
CA:100:138656 abs of Tetrahedron letters by Sahlberg et al 24(46) pp 5137–5138 1983.*
CA:109:54257 abs of Chemistry Letters by Fugami et al (11) pp 2203–2206 1987.*
CA:82:125154 abs of Petroleum Chemistry by Eisenbraun et al 18(1) pp 156–160 1973.*
CA:98:126177 abs of Journal of Organometallic Chemistry by Uemura et al 243 (1) pp 9–18 1983.*
CA:97:127156 abs of Journal of the Chemical Society Chem Comm. by Fiandanese et al (12) pp 647–649 1982.*
Fugami et al., "Carbon–Carbon Bond Formation by Cross Coupling of Enol Phosphates or Enol Triflates with Organomanganese Compounds", *Chemistry Letter*, pp. 2203–2206 (1987).

Sahlberg et al., "Synthesis of Conjugated Dienes by Nickel–Catalyzed Reactions of 1,3–Alkadien–2–YL Phosphates with Grignard Reagents", *Tetrahedron Letters*, 24:(46) pp. 5137–5138 (1993).
Karlstrom et al., "Nickel–Catalyzed Cross–Coupling of Dienyl Phosphates with Grignard Reagents in the Synthesis of 2–Substituted 1,3–Dienes", *J. Org. Chem.*, 64: pp. 1745–1749 (1999).
Takai et al., "Cross–coupling Reaction between Enol Phosphates and Organoaluminium Compounds in the Presence of Palladium (0) Ctalyst", *Bull Chem. Soc. jpn>*, 57: 108–115 (1984).
Takai et al., Carbon–Carbon Bond Formation By Cross–Coupling of Enol Phosphates with Organoaluminium Compounds Catalyzed by Palladium(O) Complex, *Tetranhedron Letters*, 21, pp. 2531–2534 (1980).
Fukamiya et al., "Conjugate addition of trialkyl aluminium and lithium benzene thiolate with enol phosphate of 2,3–dicarbonyl compound", *Chem. Ind. (London)* 17: 606–7 (1981) *Communications to the Editor*.
Sato et al., "Pd (0) Promoted Alkylation of Enol Phosphate with Organoaluminium Compounds and Its Synthetic Applications", *Tetrahedron Letters*, 22:(17) pp. 1609–1612 (1981).
Alderdice et al., "The Synthesis of the isomeric components of San Jose scale pheromone –an illustration of a stereospecific synthesis of trisubstituted alkenes", *Can. J. Chem.*, 71: pp. 1955–1963 (1993).
Asao et al., "Convenient Stereoselective Syntheses of (6E)–and (6Z)–5,6–Dimethyl–8–sily1–6–octenals", *Synthesis*, 382–6 (1990).
Hayashi et al., "Cross–Coupling of Enol Phosphates with Trimethylsilymethylmagnesium Halides Catalyzed by Nickel or Palladium Complexes; A Selective Synthesis of Allylsilanes", *Synthesis*, pp. 1001–3 (1981).
Armstrong et al., "Electrophilic cyclization of polyene allyslsilanes. Synthesis of albicanyl acetate", *Can J. Chem.*, 60: 673–5 (1982).
Danishefsky and Mantlo, "Total Synthesis of (±)–Heptelidic Acid", *J. Am. Chem. Soc.*, 110, pp. 8129–8133 (1988).
Okuda et al., "New Synthesis of Allylsilanes and Vinylsilanes by Means of phMe$_2$Si–AIEt$_2$", *Tetrahedron Letters*, 24: (19), pp. 2015–2018, (1983).

(List continued on next page.)

*Primary Examiner*—Jean F. Vollano
(74) *Attorney, Agent, or Firm*—Townsend and Townsend and Crew LLP

(57) ABSTRACT

The present invention provides a process for preparing a vinylaromatic compound comprising reacting an arylmetal reagent selected from arylmagnesium reagents and aryllithium reagents with a vinylphosphate in the presence of a palladium catalyst. The present invention also provides a process for preparing a vinylphosphate comprising reacting an enolizable ketone with a sterically hindered Grignard reagent and a halophosphate diester.

21 Claims, No Drawings

OTHER PUBLICATIONS

Fugami et al., "New Synthesis of Vinylsilanes and Allylsilanes by Cross–Coupling of $(R_3Si)_3$ MnMgMe With Alkenyl and Allylic Compounds", *Tetrahedron Letters*, 27:(19), pp. 2161–2164 (1986).

Nan and Yang, "Nickel–Catalyzed Cross–Coupling of Cyclohexenyl Phosphate and Arylboronic Acids", *Tetrahedron Letters*, 40: pp. 3321–3324 (1999).

Hayashi et al., "Nickel–Catalyzed Cross–Coupling of Aryl Phosphates with Grignard and Organoaluminium Reagents. Synthesis of Alkyl–, Alkenyl–, and Arylbenzenes from Phenols", *Tetrahedron Letters*, 22:(44), pp. 4449–4452 (1981).

Welch et al., "A New Reagent for A "One–Pot" Cyclopentenone Annelation", *Tetrahedron Letters*, 27:(10), pp. 1115–1118 (1986).

Hettrick et al., "Palladium–Catalyzed Cross–Coupling of β–(Methanesulfonyl)oxy Enones with Organostannanes", *J. Org. Chem.*, 56:(4) pp. 1489–1482 (1991).

Wu and Yang, "Nickel–Catalyzed Cross –Couplings of 4–Diethylphosphonooxycoumarins with Organozine Reagents: An Efficient New Methodology for the Synthesis of 4–Substituted Coumarins", *J. Org. Chem.*, 66: pp. 7875–7878. (2001).

Calogeropoulou et al., "Synthesis of β–Keto Phosphonates from Vinyl Phosphates via a 1,3–Phosphorus Migration", *J. Org. Chem.*, 52: pp. 4185–4190 (1987).

Lednicer et al., "Mammalian Antifertility Agents. III. 1–Aryl–2–phenyl–1,2,3,4–tetrahydro–1–naphthols, 1–Aryl–2–phenyl–3,4–dihydronaphthalenes, and Their Derivaties[1]", *J. Med. Chem.*, 9: pp. 172–176 (1966).

Lednicer et al., "Mammalian Antifertility Agents. IV. Basic 3,4–Dihydronaphthalenes and 1,2,3,4–Tetrahydro–1–naphthols [1,2]", *J. Med. Chem.*, 10: pp. 78–84 (1967).

* cited by examiner

PROCESS FOR PREPARING VINYLAROMATIC COMPOUNDS

CROSS-REFERENCES TO RELATED APPLICATIONS

Not Applicable.

STATEMENT AS TO RIGHTS TO INVENTIONS MADE UNDER FEDERALLY SPONSORED RESEARCH OR DEVELOPMENT

Not Applicable.

REFERENCE TO A "SEQUENCE LISTING," A TABLE, OR A COMPUTER PROGRAM LISTING APPENDIX SUBMITTED ON A COMPACT DISK

Not Applicable.

FIELD OF THE INVENTION

This invention relates generally to preparing vinylaromatic compounds. More specifically, it relates to preparing vinylaromatic compounds wherein the vinyl group is derived from an enolizable aldehyde or ketone and the aromatic group is derived from an arylmetal reagent. The invention also relates to preparing vinylphosphates from enolizable ketones for use in coupling reactions to prepare vinyl compounds. Vinylaromatic compounds are valuable as fine chemical intermediates and pharmaceutically active compounds. For example, nafoxidine, a vinylaromatic compound, is an estrogen receptor modulator which can be converted, via hydrogenation of the vinylic double bond, to lasofoxifene, another estrogen receptor modulator.

BACKGROUND OF THE INVENTION

A classical method for the preparation of vinylaromatic compounds is the reaction of an aldehyde or ketone bearing a hydrogen on a carbon adjacent to the carbonyl group with an arylmetal reagent to form, on acidic hydrolysis, first an alcohol then a vinylaromatic compound by acid catalyzed dehydration. This is diagrammed in the top route in Scheme 1 in which the arylmetal reagent is an aryl Grignard reagent and where R, R', R" are each hydrogen or a hydrocarbyl group, Ar is an aromatic group, and X is a halide. An alternative mode of reaction that can occur between the aldehyde or ketone and the arylmetallic reagent reactants is simple α-deprotonation of the aldehyde or ketone to form the enolate and the protonated aromatic group. On hydrolysis, the enolate returns the aldehyde or ketone starting material. This is diagramed in the bottom route in Scheme 1.

Scheme 1

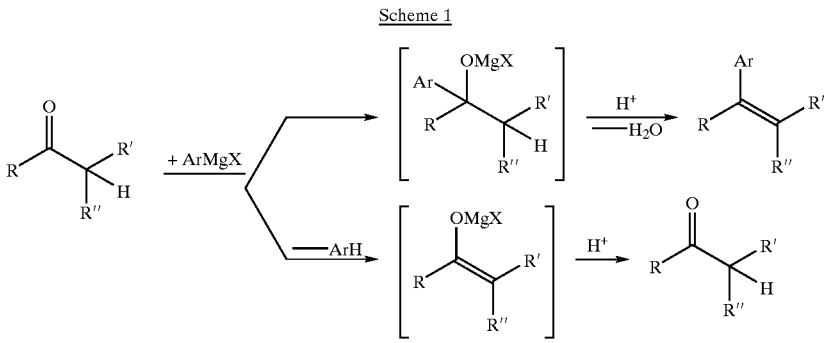

The alternative mode of reaction to form the enolate can cause not only chemical yield loss, but also recovery yield loss due to problematic separations of the desired product from the alternative products. For certain combinations of aldehydes or ketones (certain R, R', R") and aryl Grignard reagents (certain Ar), the enolization reaction so dominates as to make this method practically useless for the preparation of the desired vinylaromatic compound.

Lednicer et al., *J. Med. Chem. Soc.*, vol. 9 (1966), pp. 172–176 and Lednicer et al., *J. Med. Chem. Soc.*, vol. 10 (1967), pp. 78–84 disclose preparations of certain 1,2-diaryl-3,4-dihydronaphthalene compounds, including nafoxidine, via reactions of corresponding 2-aryl-1-tetralone compounds with aryl Grignard reagents. Lednicer et al., in *J. Med. Chem. Soc.*, vol. 12 (1969), pp. 881–885, later state, "The nucleus of this system [1,2-diaryl-3,4-dihydronaphthalenes] has usually been prepared by condensation of the appropriate 2-aryl-1-tetralone with the Grignard reagent of the aryl group that is to appear at the 1 position. Yields in this reaction have tended to be poor due to extensive enolization of the ketone by the Grignard reagent; large amounts of unreacted ketone are characteristically recovered."

U.S. Pat. No. 5,552,412 discloses preparations of nafoxidine (1-{4-[2-(pyrrolidin-N-yl)ethoxy]phenyl}-6-methoxy-2-phenyl-3,4-dihydronaphthalene) from 1-{4-[2-(pyrrolidin-N-yl)ethoxy]phenyl}-6-methoxy-3,4-dihydronaphthalene, a 1-aryl-3,4-dihydronaphthalene compound. (In the patent it is designated by the alternative name 1-{2-[4-(6-methoxy-3,4-dihydronaphthalen-1-yl)phenoxy]ethyl)pyrrolidine.) The 1-{4-[2-(pyrrolidin-N-yl)ethoxy]phenyl}-6-methoxy-3,4-dihydronaphthalene was prepared by reacting an excess of a 4-[2-(pyrrolidin-N-yl)ethoxy]phenyl cerium reagent (prepared from the corresponding aryl bromide by treating sequentially with n-butyl lithium and cerium chloride) with 6-methoxy-1-tetralone, combined at −78° C. and allowed to warm to room temperature, and subsequently acidifying the product mixture. In the ensuing workup, 34% of the 6-methoxy-1-tetralone was recovered prior to isolation of the desired 1-{4-[2-(pyrrolidin-N-yl)ethoxy]phenyl}-5 6-methoxy-3,4-dihydronaphthalene in 57% yield (See Step A in column 21).

Aldehydes and ketones can be converted to vinylphosphates by phosphorylation of their enolates. Bases that have typically been used to generate the enolates for phosphorylation include amines (e.g. triethylamine), amides (e.g. lithium diisopropylamide), alkoxides (e.g. potassium t-butoxide), and basic salts (e.g. potassium carbonate).

Vinyl phosphates have been used as reagents in coupling reactions to prepare vinyl compounds. Fugami et al., *Chem. Lett.* (1987), pp. 2203–2206 disclose reactions of certain vinylphosphates with triphenylmanganate reagent, preformed from phenyl lithium or phenyl Grignard reagent and $Li_2MnCl_4$, in the presence of a palladium catalyst provided by $Pd(PPh_3)_4$ to afford vinylbenzene compounds. Nan et al., *Tetrahedron Letters*, vol. 40 (1999), pp. 3321–3324 discloses reactions of cyclohexenylphosphate with arylboronic acid reagents in the presence of a palladium or nickel catalyst to afford cyclohexenyl aromatic compounds. Sahlberg et al., *Tetrahedron Letters*, vol. 24 (1983), pp. 5137–5138 and Sofia et al., *J. Org. Chem.*, vol. 64 (1999), pp. 1745–1749 each disclose reactions of certain 1,3-dien-2-ol phosphates with phenyl Grignard reagent in the presence of certain phosphine ligated nickel catalysts to afford 2-phenyl-1,3-diene compounds (α-vinyl-vinylbenzene compounds). Wu et al., *J. Org. Chem.*, vol. 66 (2001), pp. 7875–7878 discloses reactions of 4-diethylphosphonooxycoumarins with alkyl or aryl zinc reagents in the presence of a nickel or palladium catalyst to afford 4-alkyl or 4-aryl substituted coumarins.

Takai et al., *Tetrahedron Letters*, vol. 21 (1980), pp. 2531–2534; Takai et al., *Bull. Chem. Soc. Jpn.*, vol. 57 (1984), pp. 108–115; Fukarniya et al., *Chem. Ind.* (London), vol. 17 (1981), pp. 606–607; Sato et al., *Tetrahedron Letters*, vol. 22 (1981), pp. 1609–1612; Asao et al., *Synthesis* (1990), pp. 382–386; and Alderdice et al., *Can. J. Chem.*, vol. 71 (1993), pp. 1955–1963 disclose, in all, reactions of certain vinylphosphates with trialkyl-, trialkenyl-, or trialkynyl-aluminum reagents in the presence of a palladium, nickel, or copper catalyst to afford vinyl-alkyl, -alkenyl, or -alkynyl compounds. Hayashi et al., *Synthesis* (1981), pp. 1001–1003; Armstrong et al., *Can. J. Chem.*, vol. 60 (1982), pp. 673–675; and Danishefsky et al., *J. Am. Chem. Soc.*, vol. 110 (1988), pp.8129–8133 disclose, in all, reactions of certain vinylphosphates with trimethylsilylmethylmagnesium halide reagents in the presence of a palladium or nickel catalyst to afford allyltrimethylsilane compounds. Okuda et al. *Tetrahedron Letters*, vol. 24 (1983), pp. 2015–2018 discloses reactions of certain vinyl-phosphates with phenyldimethylsilyl-aluminum and -magnesium reagents in the presence of a palladium catalyst to afford vinylsilane compounds.

Hayashi et al., *Tetrahedron Letters*, vol. 22 (1981), pp. 4449–4452 discloses reactions of aryl phosphates with alkyl or aryl Grignard reagents in the presence of a nickel catalyst to afford alkyl-aryl compounds and biaryl compounds, respectively.

OBJECTS OF THE INVENTION

The object of this invention is to provide an effective and efficient process for the preparation of vinylaromatic compounds. A further object of this invention is to provide such a process capable of using enolizable aldehydes and ketones to provide the vinyl group in combination with using arylmetal reagents selected from arylmagnesium reagents and aryllithium reagents to provide the aromatic group. Another object of this invention is to provide a process for preparing vinylphosphates from enolizable ketones for use in coupling reactions to prepare vinyl compounds.

A further object of this invention is to provide an advantageous process for the preparation of 1-aryl-3,4-dihydronaphthalene compounds. A specific object of this invention is to provide a advantageous processes for the preparations of 1-{4-[2-(pyrrolidin-N-yl)-ethoxy]phenyl}-6-methoxy-3,4-dihydronaphthalene and nafoxidine. Other objects and advantages of the invention will become apparent to persons skilled in the art upon reading this specification.

SUMMARY OF THE INVENTION

In general terms, the present invention provides a process for preparing a vinylaromatic compound comprising reacting an arylmetal reagent selected from arylmagnesium reagents and aryllithium reagents with a vinylphosphate in the presence of a palladium catalyst.

The present invention also provides a process for preparing a vinylphosphate comprising reacting a ketone bearing a hydrogen on a carbon adjacent to the carbonyl group (that is, an enolizable ketone) with a sterically hindered Grignard reagent and a halophosphate diester. The vinylphosphate so produced is suitable to directly use, without separation or isolation, in a coupling reaction with an arylmetal reagent. In one embodiment of the present invention, the vinylphosphate so produced is reacted with an arylmetal reagent selected from arylmagnesium reagents and aryllithium reagents in the presence of a palladium catalyst to produce a vinylaromatic compound.

In one embodiment, the present invention provides an process for the preparation of 1-aryl-3,4-dihydronaphthalene compounds comprising reacting a 3,4-dihydronaphth-1-yl phosphate compound with an arylmetal reagent selected from arylmagnesium reagents and aryllithium reagents in the presence of a palladium catalyst. In one such embodiment, the 3,4-dihydronaphth-1-yl phosphate compound is produced by reacting a 1-tetralone compound with a sterically hindered Grignard reagent and a halophosphate diester. In a more specific embodiment, the present invention provides a process for preparing I-{4-[2-(pyrrolidin-N-yl)ethoxy]phenyl}-6-methoxy-3,4-dihydronaphthalene comprising reacting a 4-[2-(pyrrolidin-N-yl)ethoxy]phenylmagnesium halide reagent with a 6-methoxy-3,4-dihydronaphth-1-yl phosphate in the presence of a palladium catalyst. In one such embodiment, the 6-methoxy-3,4-dihydronaphth-1-yl phosphate is produced by reacting 6-methoxy-1-tetralone with a sterically hindered Grignard reagent and a chorophosphate diester.

BRIEF DESCRIPTION OF THE DRAWINGS

Not applicable.

DETAILED DESCRIPTION OF THE INVENTION

Unless otherwise stated, the following terms used in the specification and claims have the meanings given below:

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. "Side-reaction" is a reaction that does not ultimately lead to a production of a desired product.

"Alkyl" means a linear saturated monovalent hydrocarbon radical or a branched saturated monovalent hydrocarbon radical or a cyclic saturated monovalent hydrocarbon radical, having the number of carbon atoms indicated in the prefix. For example, $(C_1–C_6)$alkyl is meant to include methyl, ethyl, n-propyl, 2-propyl, tert-butyl, pentyl, cyclopentyl, cyclohexyl and the like. For each of the definitions herein (e.g., alkyl, alkenyl, alkoxy, aralkyloxy), when a prefix is not included to indicate the number of main chain carbon atoms in an alkyl portion, the radical or portion thereof will have twelve or fewer main chain carbon atoms. A divalent alkyl radical refers to a linear saturated divalent hydrocarbon radical or a branched saturated divalent hydrocarbon radical having the number of carbon atoms indicated in the prefix. For example, a divalent $(C_1–C_6)$alkyl is meant to include methylene, ethylene, propylene, 2-methylpropylene, pentylene, and the like.

"Alkenyl" means a linear monovalent hydrocarbon radical or a branched monovalent hydrocarbon radical having the number of carbon atoms indicated in the prefix and containing at least one double bond. For example, $(C_2–C_6)$ alkenyl is meant to include, ethenyl, propenyl, and the like.

"Alkynyl" means a linear monovalent hydrocarbon radical or a branched monovalent hydrocarbon radical containing at least one triple bond and having the number of carbon atoms indicated in the prefix. For example, $(C_2–C_6)$alkynyl is meant to include ethynyl, propynyl, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Aryl" means a monocyclic or bicyclic aromatic hydrocarbon radical of 6 to 10 ring atoms which is substituted independently with one to four substituents, preferably one, two, or three substituents selected from alkyl, alkenyl, alkynyl, halo, nitro, cyano, hydroxy, alkoxy, amino, monoalkylamino, di-alkylamino and heteroalkyl. More specifically the term aryl includes, but is not limited to, phenyl, biphenyl, 1-naphthyl, and 2-naphthyl, and the derivatives thereof.

"Aralkyl" refers to a radical wherein an aryl group is attached to an alkyl group, the combination being attached to the remainder of the molecule through the alkyl portion. Examples of aralkyl groups are benzyl, phenylethyl, and the like.

"Heteroalkyl" means an alkyl radical as defined herein with one, two or three substituents independently selected from cyano, alkoxy, amino, mono- or di-alkylamino, thioalkoxy, and the like, with the understanding that the point of attachment of the heteroalkyl radical to the remainder of the molecule is through a carbon atom of the heteroalkyl radical.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, halo, nitro, cyano, hydroxy, alkoxy, amino, acylamino, monoalkylamino, di-alkylamino, heteroalkyl, More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

In a general sense, the present invention provides a method for the preparation of a vinylaromatic compound of the formula III from an aldehyde or ketone of the formula I via a vinylphosphate of the formula II.

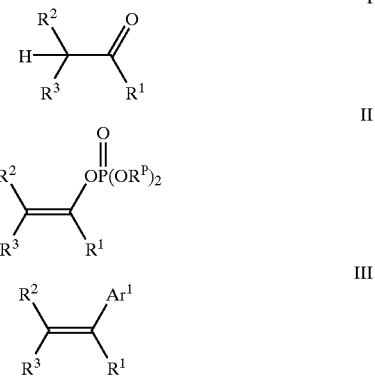

$R^P$ in formula II is hydrocarbyl, so that the vinylphosphate is a phosphate triester wherein at least one of the phosphate ester groups is a vinylphosphate ester group. Suitable hydrocarbyl groups for $R^P$, include alkyl, aryl, and aralkyl groups. Preferred $R^P$ are methyl, ethyl, and phenyl. Alternatively, one or both of the hydrocarbyl groups $R^P$ can be another identical vinyl group.

$R^1$ in formulas I, II, and III is hydrogen (for an aldehyde) or a hydrocarbyl group (for a ketone). $R^2$ and $R^3$ in formulas I, II, and III can be independently hydrogen, a hydrocarbyl group hydrocarbyl, or any substituent that does not interfere with the reaction chemistry of the invention. Suitable hydrocarbyl groups for $R^1$, $R^2$, and $R^3$ include acyclic, cyclic, and heterocyclic hydrocarbyl groups, include saturated and unsaturated hydrocarbyl groups, include alkyl, heteroalkyl, aryl, heteroaryl, aralkyl, alkenyl, and alkynyl groups, as well as combinations thereof, and can be optionally substituted with one or more substituents that do not interfere with the reaction chemistry of the invention. Combinations of $R^1$, $R^2$, and $R^3$ can be linked together in one or more cyclic structures.

$Ar^1$ in formula II is an optionally substituted aryl group or heteroaryl group as defined above.

Suitable substituents for $R^2$ and $R^3$, for substituents on hydrocarbyl groups for $R^1$, $R^2$, and $R^3$, and for substituents on aryl group or heteroaryl group $Ar^1$ are substituents that do not interfere with the reaction chemistry. The vinylphosphate of formula II should not comprise any other substituent that is reactive to the aryl metal reagent unless it is intended to also react. One skilled in the art will recognize suitable and unsuitable substituents which can be different depending on the choice of reagents (e.g. arylmagnesium or aryllithium reagents) and other specific reaction conditions. Suitable substituents include, by example, alkoxy, aryloxy, tertiary amino, and halo. However, the aldehyde or ketone of formula I will typically be void of any other ketone or aldehyde substituent unless it is intended to also react.

The vinylphosphate can be prepared by reaction of the corresponding aldehyde or ketone with a halophosphate diester of the formula $XP(=O)(OR^P_2)$, wherein X is a halide, preferably chloride or bromide and most preferably chloride, and $R^P$ is defined as above, in the presence of a base. Suitable bases for the preparation of vinylphosphates are known in the art and include amines (e.g. triethylamine), amides (e.g. lithium diisopropylamide), alkoxides (e.g. potassium t-butoxide), and basic salts (e.g. potassium carbonate). The vinylphosphate prepared using such bases should be preferably separated from the neutralized base coproduct (e.g. triethylammonium chloride from triethylamine, alcohol from alkoxide) prior to its reaction with the arylmetal reagent to form the vinylaromatic compound. Such neutralized bases comprise an active hydrogen and, if still present with the vinylphosphate, would quench an equivalent of arylmetal reagent to return the aryl-hydrogen compound.

The present invention provides a process for preparing the vinylphosphate by reacting a ketone with the halophosphate diester using a sterically hindered Grignard reagent for the base. The steric hindrance of the Grignard reagent substantially impedes its ability to react by addition to the ketone (the top route in Scheme 1) and thereby substantially favors its reaction to α-deprotonate and enolize the ketone (the bottom route in Scheme 1). The enolate so formed then reacts with the halophosphate to form the vinylphosphate. Because the neutralized form of the sterically hindered Grignard reagent comprises a new, inert C-H bond, instead of an active hydrogen, the resulting vinylphosphate is suitable to use directly, without any separations or isolation, in a coupling reaction with an arylmetal reagent.

Suitable sterically hindered Grignard reagents have the formula $R^4MgX$ wherein $R^4$ is a sterically hindered hydrocarbyl group and X is a halide, preferably chloride or bromide. It will be understood that the for the purpose of this invention, the "sterically hindered" nature of the Grignard reagent is defined functionally in relation to the specific ketone which it is to be preferentially deprotonated and enolized for phosphorylation. Thus, a ketone with lesser steric hindrance about its carbonyl group will require a Grignard reagent with greater steric hindrance in its $R^4$ hydrocarbyl group in order for the Grignard reagent to preferentially deprotonate and enolize the ketone, and vice versa. Typically, an aldehyde is not sufficiently sterically hindered about its carbonyl group for its vinylphosphate to be prepared using a Grignard reagent for the base. For a specific ketone, this can be determined by routine phosphorylation experiments such as those illustrated in the Examples. Preferably, the sterically hindrance of the Grignard reagent is sufficient to provide at least a 75% yield, and more preferably at least a 90% yield, of the vinylphosphate from the specific ketone.

Generally, the $R^4$ hydrocarbyl group in the sterically hindered Grignard reagent is selected from secondary alkyl groups (e.g. isopropyl), tertiary alkyl groups (e.g. tertiary butyl), and ortho-alkyl substituted aryl groups, preferably ortho,ortho-dialkyl substituted aryl groups (e.g. mesityl and 2,4,6-tri-t-butylphenyl). Mesityl Grignard reagent is generally preferred with most ketones.

The phosphorylation reaction of the ketone with the halophosphate diester using a sterically hindered Grignard reagent can be conducted without solvent or with an additional solvent that is reaction-inert. By reaction-inert solvent is meant a solvent system which does not react with the reactants or products of the reaction, or react unfavorably with the catalyst. The term solvent system is used to indicate that a single solvent or a mixture of two or more solvents can be used. Representative solvents are aromatic hydrocarbons such as benzene, toluene, xylene; aliphatic hydrocarbons such as pentane, hexane, heptane; dialkyl ethers; and cyclic ethers, and mixtures thereof. The solvent system used need not bring about complete solution of the reactants. Preferred solvents in the solvent system are ether solvents, including diethyl ether, diisopropyl ether, dibutylether, methyl-t-butylether, dimethoxyethane, diglyme, dibutyldiglyme, tetrahydrofuran, dioxane, and the like. It is generally preferred that the solvent system is anhydrous.

The ratios of the halophosphate diester, the ketone, and the sterically hindered Grignard reagent can be varied. Either reactant can be the limiting reactant and this choice can respond to other considerations, such as which is the more costly reactant to provide, which product of the unreacted excess reagent is more readily separated from the vinylaromatic product, or, if the vinylphosphate is to be used directly in a coupling reaction with an arylmetal reagent, which unreacted excess reagent is more readily tolerated in the subsequent coupling reaction. Generally the ratio of equivalents of the halophosphate diester to the ketone is in the range from 0.5:1 to 2:1. In typical embodiments, this ratio is in the range 1:1 to 1.5:1. When the vinylphosphate is to be used directly in a coupling reaction with an arylmetal reagent, without any separations or isolation, a modest excess of the halophosphate diester to the ketone is often preferred to provide substantially complete conversion of the ketone but with only a minimal amount of unreacted halophosphate diester entering the subsequent coupling reaction. Generally the ratio of equivalents of the sterically hindered Grignard reagent to the ketone is in the range from 0.5:1 to 2:1. In typical embodiments, this ratio is in the range 1:1 to 1.5:1 Typically, a modest excess of the sterically hindered Grignard reagent to the ketone is often preferred to provide substantially complete conversion of the ketone.

In typical embodiments, the phosphorylation reaction is suitably conducted at a temperature of from about 0° C. to 100° C., although higher temperature can be used in some embodiments.

The order of addition of the phosphorylation reaction components can be varied. All the reaction components can be mixed at a temperature below that at which reaction occurs, in any order, and then heated to the reaction temperature. Alternatively, one or more of the components can be added to a mixture of the other components that is at the desired reaction temperature. It is generally preferred to add the sterically hindered Grignard reagent last to avoid side reactions of the enolate anion in the absence of the chlorophosphate. The preferred order and manner of addition for any specific embodiment can be determined by routine experimentation with a view towards both reaction performance and chemical engineering considerations.

The vinylaromatic compound is prepared by reacting the vinylphosphate compound with an arylmetal reagent selected from arylmagnesium reagents and aryllithium reagents in the presence of a palladium catalyst. Suitable arylmagnesium reagents are selected from the group consisting of arylmagnesium salts, diarylmagnesium compounds, or mixtures thereof. Arylmagnesium salts have the general formula $Ar^1MgY$, wherein $Ar^1$ is an an optionally substituted aryl group or heteroaryl group as defined above and Y is an inorganic or organic salt anion. Preferred arylmagnesium salts are arylmagnesium halides, also known as aryl Grignard reagents, of the general formula $Ar^1MgX$, wherein X is a halide anion. Especially preferred are arylmagnesium chloride and arylmagnesium bromide reagents. Diaryl magnesium compounds have the general formula $Ar^1_2Mg$. Arylmagnesium halides and diarylmagnesium compounds can be prepared from arylhalides and magnesium by methods known in the art.

Suitable aryllithium reagents are aryllithium compounds of the general formula $Ar^1Li$, wherein $Ar^1$ is as defined above. Aryllithium compounds can be prepared by methods known in the art.

In one embodiment, the present invention provides a method for the preparation of a 1-aryl-3,4-dihydronaphthalene compound of the formula VI from a 1-tetralone compound of the formula IV via a 3,4-dihydronaphth-1-yl phosphate compound of the formula V.

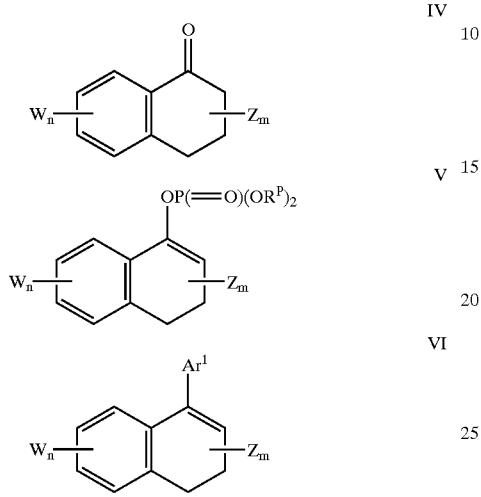

$R^P$ in formula V and $Ar^1$ in formula VI are defined as above. In this embodiment, $Ar^1$ is preferably a phenyl or substituted phenyl group. Preferred substituted phenyl groups include para-alkoxy substituted phenyl groups, most preferably wherein the alkoxy substituent is a 2-dialkylaminoethoxy substituent of the formula $R^5R^6NCH_2CH_2$—, wherein $R^5$ and $R^6$ are hydrocarbyl groups defined as for $R^2$ and $R^3$ above.

W in formulas IV, V and VI is a substituent on one or more of the 5, 6, 7, or 8 positions of the 1-tetralone (Formula IV) or 3,4-dihydronaphthalene (formulas V and VI) ring system, selected from substituents that do not interfere with the reaction chemistry of the invention. These are known to persons skilled in the art and can be determined by routine experimentation. Examples of suitable substituents are the same as $R^2$ and $R^3$ described above. The subscript n in the formulas IV, V, and VI is an integer from 0 to 4. Preferably n=1 and most preferably the substituent W is on the 6-position of the ring system. A particularly preferred substituent W is methoxy. When n=0, no substituent W is present in the formula. When n is greater than 1, the W substituents can be the same or different and are selected independently of each other.

Z in formulas IV, and V is a substituent on one or more of the 2, 3 or 4 positions of the 1-tetralone (Formula IV) or 3,4-dihydronaphthalene (formulas V and VI) ring system, and is defined as for W above. The subscript m is an integer from 0 to 3, preferably 0 or 1. When m=0, no substituent Z is present in the formula. When m=1, the substituent is preferably on the 2 position of the ring system. Particularly preferred substituents on the 2 position are aryl groups and heteroaryl groups as defined above, and most preferably phenyl. When m is greater than 1, the Z substituents can be the same or different and are selected independently of each other.

In one such embodiment, the present invention provides a process for preparing 1-{4-[2-(pyrrolidin-N-yl)ethoxy]phenyl}-6-methoxy-3,4-dihydronaphthalene (formula IX) comprising reacting a 4-[2-(pyrrolidin-N-yl)ethoxy]phenylmagnesium halide (formula VIII, wherein X is as defined above) with a 6-methoxy-3,4-dihydronaphth-1-yl phosphate compound (formula VII, wherein $R^P$ is as defined above) in the presence of a palladium catalyst. The 6-methoxy-3,4-dihydronaphth-1-yl phosphate compound can be produced from 6-methoxy-1-tetralone.

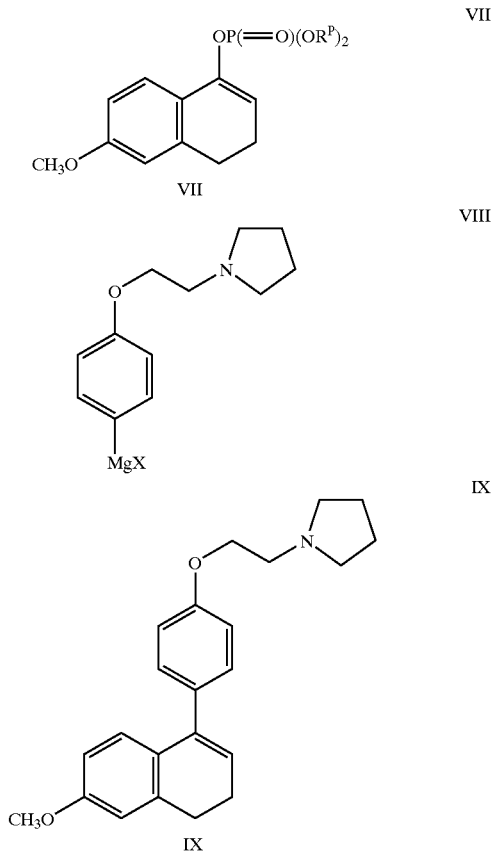

Suitable palladium catalysts include those provided by palladium compounds and salts, in particular palladium(0) compounds and palladium(II) compounds and salts. Preferably, the palladium catalyst also comprises a ligand. Suitable ligands include monodentate, bidentate, and tridentate ligands comprising nitrogen or phosphorus as ligating atom. Preferred ligands include triorganophosphines, triorganophosphites, and aromatic nitrogen heterocycle ligands. Examples of preferred ligands include triarylphosphines (e.g. triphenylphosphine), bidentate bis (diarylphosphino) compounds (e.g. 1,1'-bis (diphenylphosphino)ferrocene), trialkylphosphites (e.g. triisopropylphosphite), and pyridine-type ligands (e.g. pyridine, bipyridine). Particular ligands include those illustrated in the working Examples herein.

Suitable and optimal ratios of the ligand to catalyst metal depend on a number of other parameters, including the identity of the ligand, the concentration of the catalyst, the reaction temperature, the reactivity of the reactants, the solvent, and the like, and can be readily determined by routine experimentation. Typically the ratio of the ligand to the catalyst metal is in the range of 1:1 to 4:1. However, the amount of ligand in the reaction mixture can be in excess of the maximum ratio that could be bound to the catalyst metal.

The active catalyst can be prepared in advance of its introduction to the reaction mixture, or can be generated in the reaction mixture. It is believed that the active catalyst in the reaction is a palladium(0) catalyst. The active catalyst can be provided by a preformed ligated palladium(0) compound (e.g. tetrakis(triphenylphosphine)palladium(0)) or can be provided by combining in solution, either ex situ or in situ to the reaction mixture, a suitable ligand with a suitable palladium(0) source (e.g. tris(dibenzylideneacetone)palladium(0)). When the catalyst is provided by a palladium(II) compound or salt, the active catalyst is believed to be generated by reduction of the palladium(II) compound or salt either ex situ or in situ to the reaction mixture. Generally, the arylmetal reagent is capable of reducing the palladium(II) to generate the active catalyst in situ. This can be determined by routine experimentation. Suitable reductants for ex situ generation of the active catalyst from palladium(II) sources are known in the art and include organomagnesium halide reagents (e.g. methylmagnesium halide) and various hydride reagents (e.g. sodium bis(2-methoxyethoxy)-aluminum dihydride). Preferably the palladium(II) is combined with ligand prior to its reduction. The palladium(II) can be provided as a preformed ligated palladium(II) compound (e.g. dichlorobis(triphenylphosphine)palladium(II)) or can be provided by combining in solution a suitable ligand with a suitable palladium(II) compound (e.g. dichlorobis(acetonitrile)palladium(II)) or salt. Suitable palladium(II) salts include the salts having the general formula $PdY'_2$, wherein Y' is an inorganic or organic salt anion. Preferred palladium(II) salts include the chlorides, bromides, carboxylates (e.g. formate, acetate, stearate) and acetylacetonates. Generally, anhydrous palladium salts are preferred.

The coupling reaction of the arylmetal reagent with the vinylphosphate can be conducted without solvent or with an additional solvent that is reaction-inert. By reaction-inert solvent is meant a solvent system which does not react with the reactants or products of the reaction, or react unfavorably with the catalyst. The term solvent system is used to indicate that a single solvent or a mixture of two or more solvents can be used. Representative solvents are aromatic hydrocarbons such as benzene, toluene, xylene; aliphatic hydrocarbons such as pentane, hexane, heptane; dialkyl ethers; and cyclic ethers, and mixtures thereof. The solvent system used need not bring about complete solution of the reactants. Preferred solvents in the solvent system are ether solvents, including diethyl ether, diisopropyl ether, dibutylether, methyl-t-butylether, dimethoxyethane, diglyme, dibutyldiglyme, tetrahydrofuran, dioxane, and the like. It is generally preferred that the solvent system is anhydrous.

The ratio of the arylmetal reagent to the vinylphosphate can be varied. Either reactant can be the limiting reactant and this choice can respond to other considerations, such as which is the more costly reactant to provide and which product of the unreacted excess reagent is more readily separated from the vinylaromatic product. Generally the ratio of equivalents of arylmetal reagent to moles of vinylphosphate ranges from 0.5:1 to 2:1. (One mole of diarylmagnesium reagent is counted as two equivalents of arylmagnesium reagent.)

In typical embodiments, this ratio is in the range 1:1 to 1.5:1. A modest excess of arylmetal reagent over vinylphosphate is often preferred to compensate for side reactions that nonselectively deplete the arylmetal reagent; for example, biaryl coupling.

In the coupling reaction of the arylmetal reagent with the vinylphosphate, the palladium catalyst is present in catalytic amounts, meaning less than stoichiometric relative to the reactants. The mole ratio of the catalyst to the vinylphosphate to be reacted can be varied, but should be a catalytic ratio of about 1:10 or less. The minimum amount of catalyst relative to the vinylphosphate depends on the activity of the specific catalyst composition, the specific vinylphosphate and arylmetal reagent to be reacted, the reaction temperature, the concentration of the reactants and catalyst in the solution, and the maximum time allowed for completion of the reaction, and can be readily determined by routine experimentation. In typical embodiments, a suitable mole ratio of the palladium catalyst to vinylphosphate is in the range of 1:10,000 to 1:10.

In typical embodiments, the coupling reaction is suitably conducted at a temperature of from about 20° C. to 100° C., although higher temperature can be used in some embodiments.

The order of addition of the coupling reaction components can be varied. All the reaction components can be mixed at a temperature below that at which reaction occurs, in any order, and then heated to the reaction temperature. Alternatively, one or more of the components can be added to a mixture of the other components that is at the desired reaction temperature. For larger scale operation of the process, it is generally preferred to gradually add either the arylmetal reagent or the vinylphosphate to a mixture of the other components at the desired reaction temperature in order to control the exothermic heat release of the reaction by the rate of the addition. The preferred order and manner of addition for any specific embodiment can be determined by routine experimentation with a view towards both reaction performance and chemical engineering considerations.

The vinylaromatic compound can be separated from the reaction mixture and recovered by known methods.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Example 1

This Example illustrates the process of the invention wherein a ketone-derived vinylphosphate is reacted with an arylmagnesium reagent in the presence of palladium catalyst comprising a phosphine ligand to produce a vinylaromatic compound.

A solution of 0.330 g (1.00 mmol) 1-cyclohexen-1-yl diphenyl phosphate (reference: *J. Org. Chem.* vol. 52 (1987), pp. 4185–41980), 0.092 g (0.50 mmol) tridecane (internal GC standard), and 7 mg (0.01 mmol) dichlorobis(triphenylphosphine)palladium in 2 mL THF (tetrahydrofuran) was heated to 65° C. and treated dropwise with 0.60 mL (1.25 mmol) 2.08 M phenylmagnesium chloride in THF. After heating at 65° C. for 1 h (hour), a sample was withdrawn from the reaction and quenched in a mixture of ether and aqueous 1 M sodium citrate. Analysis of the organic phase by GC (gas chromatography) showed the presence of 0.81 mmol 1-phenyl-1-cyclohexene (81% chemical yield on 1-cyclohexen-1-yl diphenyl phosphate) and 0.02 mmol (2%) unreacted 1-cyclohexen-1-yl diphenyl phosphate.

Comparative Example 1

This Comparative Example illustrates the reaction of a vinylphosphate with an arylmagnesium reagent in the absence of a catalyst.

The procedure was identical to Example 1 with the exception that the dichlorobis(triphenylphosphine) palladium was omitted. The GC analysis showed 0.42 mmol (42%) unreacted 1-cyclohexen-1-yl diphenyl phosphate, 0.20 mmol (20%) cyclohexanone, 0.18 mmol (18%) 1-cyclohexen-1-yl diphenyl phosphite, 0.22 mmol triphenylphosphine oxide, and no detectable 1-phenyl-1-cyclohexene.

Example 2

This Example illustrates the process of the invention wherein an aldehyde-derived vinylphosphate is reacted with an arylmagnesium reagent in the presence of palladium catalyst comprising a phosphine ligand to produce a vinylaromatic compound (in this example, a stilbene).

2-Phenylvinyl diphenyl phosphate was prepared by treating a solution of 4.6 mL (22 mmol) diphenyl chlorophosphate and 3.6 mL (24 mmol) 1,8-diazabicyclo[5.4.0]undec-7-ene in 20 mL methylene chloride 0° C. with 2.6 mL (20 mmol) phenylacetaldehyde (90% purity. The solution was stirred at 0° C. for 6 h, poured into a mixture of water and ether (75 mL each), and the organic phase was extracted twice with 0.1 N HCl (50 mL each) and then washed with brine (25 mL). The organic phase was then dried over MgSO₄, filtered, and concentrated. Distillation using a Kugelrohr apparatus (225° C./0.1 torr) provided 6.4 g 2-phenylvinyl diphenyl phosphate (90% yield) as an approximately equal mixture of E and Z isomers.

A solution of 0.704 g (2.00 mmol) of the diphenyl 2-phenylvinylphosphate (E/Z mixture), 0.24 mL (1.0 mmol) tridecane (internal GC standard), and 14 mg (0.01 mmol) dichlorobis(triphenylphosphine)palladium in 2 mL THF was treated at room temperature with 2.50 mL (2.50 mmol) 1.00 M phenylmagnesium chloride in THF. After stirring for 1 h at room temperature, a sample was withdrawn from the reaction and quenched in a mixture of ether and aqueous 1 M sodium citrate. Analysis of the organic phase by GC showed the presence of 0.50 mmol trans-stilbene (25% yield ), 0.17 mmol cis-stilbene (9% yield), and 0.14 mmol (7%) unreacted 2-phenylvinyl diphenyl phosphate.

Examples 3–8

These Example illustrate the process of the invention wherein an enolizable ketone is reacted with a sterically hindered Grignard reagent and a halophosphate diester to produce a vinylphosphate.

A solution of 2.0 mmol tetralone (0.27 mL 1-tetralone; 0.26 mL 2-tetralone) and 0.46 mL (2.2 mmol) of diphenyl chlorophosphate in 2 mL THF was cooled to 0° C. and treated with 2.04 mmol of Grignard reagent in THF (1.89 mL 1.08 M mesitylmagnesium bromide; 1.02 mL 2.00 M isopropylmagnesium chloride; 2.04 mL 1.00 M t-butylmagneisum chloride). The solution stirred at 0° for 15 min, and allowed to warm to room temperature with stirring for an additional 30 min. Tridecane (0.24 mL; 1.0 mmol; internal GC standard) was added and a sample was withdrawn and hydrolyzed in a mixture of ether and aqueous 1 M sodium citrate. GC analysis of the organic phase showed the conversion of the tetralone and the chemical yield of the vinyl phosphate product (3,4-dihydronaphthalene-1-yl diphenyl phosphate from 1-tetralone; 3,4-dihydronaphthalene-2-yl diphenyl phosphate from 2-etralone) given in Table 1.

TABLE 1

| Example | tetralone | Grignard* | conv. (%) | yield (%) |
| --- | --- | --- | --- | --- |
| 3 | 2-tetralone | iPrMgCl | 100 | 97 |
| 4 | 2-tetralone | t-BuMgCl | 98 | 98 |
| 5 | 2-tetralone | MesMgBr | 100 | 97 |
| 6 | 1-tetralone | iPrMgCl | 65 | 28 |
| 7 | 1-tetralone | t-BuMgCl | 82 | 14 |
| 8 | 1-tetralone | MesMgBr | 100 | 93 |

*iPr = isopropyl; tBu = tertiary butyl; Mes = mesityl

Example 9

This Examples illustrates the process of the invention wherein an enolizable ketone is reacted with a sterically hindered Grignard reagent and a halophosphate diester to produce a vinylphosphate.

A solution of 0.52 mL (5.0 mmol) cyclohexanone and 1.14 mL (5.50 mmol) diphenyl chlorophosphate in 2 mL THF was treated with 15.6 mL (7.0 mmol) 0.45 M 2,4,6-tri-t-butylphenylmagnesium bromide in THF and stirred at room temperature for 24 hours. Tridecane (0.61 mL; 2.5 mmol; internal GC standard) was added and a sample was withdrawn and hydrolyzed in a mixture of ether and aqeous 1M sodium citrate. GC analysis of the organic phase showed 93% conversion of the cyclohexanone and 78% chemical yield of 1-cyclohexen-1-yl diphenyl phosphate.

Example 10

This Example illustrates the process of the invention wherein a 1-tetralone is converted to a 3,4-dihydronaphth-1-yl phosphate using a sterically hindered Grignard reagent and this vinylphosphate is used directly, without separation, to produce a 1-aryl-3,4-dihydro-naphthalene compound by reaction with an arylmagnesium reagent in the presence of a palladium catalyst.

20.0 mL (20.4 mmol) 1.02 M mesitylmagnesium bromide in THF was added over 10–15 minutes to a solution of 2.66 mL (20.0 mmol) 1-tetralone and 4.56 mL (22.0 mmol) diphenyl chlorophosphate in 4 mL THF at 0° C. The solution was stirred at 0° for 30 min, allowed to warm to room temperature, and then stirred for an additional 30 min. The reaction mixture was then treated with 0.140 g (1 mol%) dichlorobis(triphenylphosphine)palladium and warmed to 65°. 11.5 mL (24.0 mmol) 2.08 M phenylmagnesium chloride in THF was added over 5–10 minutes, resulting in a gentle reflux of the solvent. After stirring at 65° for 30 min, the mixture was cooled to room temperature and poured into a mixture of 3 N HCl (30 mL) and pentane (30 mL). The phases were separated, and the aqueous portion was extracted with pentane (25 mL). The combined organic phase was washed sequentially with 3 N HCl (15 mL), 3 N NaOH (twice, with 15 mL each time), and brine (20 mL). The resulting organic phase was dried (MgSO₄), concentrated, and then distilled using a Kugelrohr apparatus (oven temp=120–150° C.); 0.1 torr) to provide 3.51 g 1-phenyl-3,4-dihydronaphthalene (85% yield on 1-tetralone).

Example 11

This Example illustrates the process of the invention wherein 2-tetralone is converted, via a vinylphosphate, to a 2-aryl-3,4-dihydronaphthalene compound.

The procedure was identical to Example 10 with the exception that 2.64 mL (20.0 mmol) of 2-tetralone was used instead of 1-tetralone. The Kugelrohr distillation (oven temp=140–170° C.; 0.1 torr) provided 3.76 g 2-phenyl-3,4-dihydronaphthalene (91% yield on 2-tetralone).

Comparative Example 2

This Example illustrates the preparation of a 2-aryl-3,4-dihydronaphthalene compound by the direct reaction of an arylmagnesium reagent with 2-tetralone.

1.32 mL (10.0 mmol) 2-tetralone in 5 mL of THF was added to a solution of 5.77 mL (12.0 mmol) 2.08 M phenylmagnesium chloride in THF at 0° C. The mixture was allowed to warm to room temperature, and was then stirred for an additional 1 hour. Tridecane (1.22 mL; 5.00 mmol; internal GC standard) was added, the mixture was cooled to 0°, 10 mL of 6N HCl was added. The mixture was heated to 65° and vigorously stirred for 4 hours. The mixture was then cooled to room temperature and diluted with toluene. GC analysis of the organic phase showed the presence of 2.9 mmol 2-phenyl-3,4-dihydronaphthalene (29% yield on 2-tetralone) and 4.6 mmol 2-tetralone (46% recovery). No benzylic alcohol intermediate from addition of the arylmagnesium reagent to the ketone was detected, indicating that its dehydration to the vinylaromatic had been completed by the warm acid treatment.

The recovery of 2-tetralone (46%) is indicative of its propensity towards enolization by the arylmagnesium reagent in competition with the desired addition of the aryl group to the carbonyl to provide, after dehydration, the vinylaromatic. In comparison, Example 11 demonstrates a substantially higher yield of the vinylaromatic compound is obtained from 2-tetralone via the process of the present invention wherein the 2-tetralone is converted to a vinylphosphate and the vinylphosphate is reacted with the arylmagnesium reagent in the presence of a palladium catalyst.

Example 12

This Example illustrates the process of the invention wherein 2-indanone is converted via a vinylphosphate to a 2-aryl-indene compound.

The procedure is identical to Example 10 with the exceptions that 2.64 g (20.0 mmol) 2-indanone was used instead of 1-tetralone and the residue from the concentrated organic phase was recrystallized from 200 mL of 90:5:5 ethanol:isopropanol:methanol at 0° C., filtered and dried to obtain 2.34 g 2-phenylindene (61% yield on 2-indanone).

Example 13

This Example illustrates the process of the invention wherein an aryllithium reagent is used to produce a 1-aryl-3,4-dihydronaphthalene compound from a 3,4-dihydronaphth-1-yl phosphate.

The reaction procedure was identical to Example 10 at one-half scale, with the exceptions that 6.45 mL (12.0 mmol) 1.86 M phenyllithium in cyclohexane-ether was used instead of phenylmagnesium chloride in THF. After the stirring for 30 min of heating at 65°, tridecane (1.22 mL; 5.00 mmol; internal GC standard) was added to the reaction mixture and a sample was withdrawn and hydrolyzed in a mixture of aqueous 1 M sodium citrate and ether. GC analysis of the organic phase showed the presence of 6.5 mmol 1-phenyl-3,4-dihydronaphthalene (65% yield based on 1-tetralone).

Example 14

This Example illustrates the process of the invention using a vinyl dialkyl phosphate triester, whereas the preceding Examples used a vinyl diaryl phosphate triester.

The reaction procedure was identical to Example 11 at one-half scale, with the exceptions that 1.59 mL (11.0 mol) diethyl chlorophosphate was used instead of diphenyl chlorophosphate and the reaction mixture was stirred for 1 hour at 65° C. Workup and analysis of a reaction sample as in Example 13 showed the presence of 7.6 mmol 2-phenyl-3,4-dihydronaphthalene (76% yield on 2-tetralone).

Example 15

This Example illustrates the process of the invention using a sterically hindered alkyl Grignard reagent to form the vinylphosphate, whereas the preceding Examples used a sterically hindered ortho-alkylphenyl Grignard reagent The reaction procedure was identical to Example 11 at one-half scale, with the exception that 5.10 mL (10.2 mmol) 2.00 M isopropylmagnesium chloride in THF was used instead of mesitylmagnesium bromide. Workup and analysis of a reaction sample as in Example 13 showed the presence 8.1 mmol 2-phenyl-3,4-dihydronaphthalene (81% yield on 2-tetralone).

Example 16

This Example illustrates the process of the invention using another aryl group in the arylmetal reagent, whereas the preceding Examples used phenyl group.

The reaction procedure was identical to Example 11 at one-half scale, with the exception that 13.6 mL (12.0 mmol) 0.88 M p-tolylmagnesium bromide in THF was used instead of phenylmagnesium bromide in THF. Workup and analysis of a reaction sample as in Example 13 showed the presence of 8.2 mmol 2-(p-tolyl)-3,4-dihydronaphthalene (82% yield on 2-tetralone).

Example 17

This Example illustrates the invention with another ketone via its vinylphosphate.

The reaction procedure was identical to Example 16 with the exception that 1.74 g (10.0 mmol) 2-phenylcyclohexanone was used instead of 2-tetralone. After stirring for one hour at 65° C., the workup and analysis of a reaction sample showed the presence of 5.8 mmol 1-(p-tolyl)-2-phenylcyclohexene (58% yield on 2-phenylcyclohexanone).

Example 18

This Example illustrates the invention with another ketone via its vinylphosphate.

The reaction procedure was identical to Example 16 with the exception that 1.48 mL (10.0 mmol) 1-phenyl-2-butanone was used instead of 2-tetralone. The workup and analysis of a reaction sample showed the presence of 6.5 mmol 1,2-diphenyl-1-butene, presumed to be the E isomer (65% yield on 1-phenyl-2-butanone).

Example 19

This Example illustrates the invention with another ketone via its vinylphosphate.

The reaction procedure was identical to Example 16 with the exception that 0.88 mL (10.0 mmol) cyclopentanone was used instead of 2-tetralone and its reaction with the mesitylmagnesium bromide and diphenylchlorophosphate was initiated at −78° C., then after 15 min allowed to warm to 250° C. The workup and analysis of a reaction sample from the subsequent catalytic coupling reaction showed the presence of 5.8 mmol of 1-phenylcyclo-pentene (58% yield on cyclopentanone).

Example 20

This Example illustrates the process of the invention for the preparation of 1-{4-alkoxyphenyl}-6-methoxy-3,4-dihydronaphthalene from 6-methoxy-1-tetralone via its conversion to a 6-methoxy-3,4-dihydronaphth-1-yl phosphate compound and reaction of the 6-methoxy-3,4-dihydronaphth-1-yl phosphate compound with a 4-alkoxyphenylmagnesium halide in the presence of a palladium catalyst.

A solution of 3.09 g (17.5 mmol) 6-methoxy-1-tetralone in 3 mL of THF was cooled to −10° C. and sequentially treated with 5.17 g (19.3 mmol) diphenyl chlorophosphate and 18.3 mL (19.3 mmol) 1.05 M 2-mesitylmagnesium bromide in THF. The temperature during addition of this Grignard reagent was kept below 10° C. (The initially resulting slurry became homogeneous after ca one-fourth of the Grignard had been added). The resulting solution of 6-methoxy-3,4-dihydronaphth-1-yl diphenyl phosphate was then warmed to room temperature and 0.074 g (0.105 mmol; 0.6 mol%) dichlorobis(triphenylphosphine)palladium was added as a solid. The mixture was then heated to reflux, and a solution of 19.3 mmol 4-(2-pyrrolidin-N-yl) ethoxyphenylmagnesium bromide, 1.30 M THF (prepared from 0.512 g (21.1 mmol) of Mg and 5.21 g of the corresponding aryl bromide), was added dropwise over 20 minutes. After the addition was complete, the reaction mixture was stirred at reflux for an additional 30 min and then cooled to room temperature. The reaction mixture was then poured into a mixture of 35 mL each of MTBE (methyl t-butyl ether) and aqueous 1 M sodium citrate, and the mixture was vigorously stirred for 15 min. The aqueous phase was drained from the mixture, and the remaining organic phase treated with 35 mL of 6 N NaOH. The resulting mixture was then vigorously stirred at 50° C. for 3 h, then cooled to room temperature. An additional 35 mL each of MTBE and water were added in order to break the emulsion that had formed. The aqueous phase was discarded and the remaining organic phase was extracted twice with 10.5 mL of 3 N HCl. The combined acidic aqueous extracts were diluted with 15 mL of water and then extracted twice with 10 mL chlorobenzene. The combined chlorobenzene extracts were extracted twice with 20 mL of 0.5 N HCl, and then once with 20 mL of brine. The organic phase was then concentrated by distillation at atmospheric pressure, with a total of 9 mL of distillate being collected (2 mL of this distillate was water). The remaining solution in the distillation pot was then allowed to cool slowly with stirring to room temperature (at about 55° C. a flocculent solid separated from the solution), and then cooled further to 0–5° C. The mixture was held at 0–5° for 1 h, then the solid was collected by filtration and washed with a small amount of MTBE. Drying under reduced pressure gave 5.39 g the hydrochloride salt of 1-{4-[2-(pyrrolidin-N-yl)ethoxy]-6-methoxy-3,4-dihydronaphthalene as a white solid (80% yield on 6-methoxy-1-tetralone).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for the preparation of a vinylaromatic compound comprising contacting a vinylphosphate with an arylmetal reagent selected from arylmagnesium reagents and aryllithium reagents in the presence of a palladium catalyst, under conditions sufficient for coupling to occur between the vinyl portion of said vinylphosphate and an aryl portion of said arylmetal reagent.

2. The process of claim 1 wherein the arylmetal reagent is an arylmagnesium halide.

3. The process of claim 1 wherein the palladium catalyst comprises a phosphine ligand.

4. The process of claim 1 wherein the vinylphosphate is prepared by a process comprising reacting an enolizable ketone with a sterically hindered Grignard reagent and a halophosphate diester.

5. The process of claim 4 wherein the sterically hindered Grignard reagent is sufficient to provide at least a 75% yield of the vinylphosphate.

6. The process of claim 4 wherein the sterically hindered Grignard reagent is selected from the group consisting of secondary alkyl Grignard reagents, tertiary alkyl Grignard reagents and ortho-alkyl substituted phenyl Grignard reagents.

7. The process of claim 4 wherein the arylmetal reagent is an aryl magnesium halide.

8. The process of claim 4 wherein the palladium catalyst comprises a phosphine ligand.

9. The process of claim 4 wherein the sterically hindered Grignard reagent is sufficient to provide at least a 75% yield of the vinylphosphate and is selected from the group consisting of secondary alkyl Grignard reagents, tertiary alkyl Grignard reagents and ortho-alkyl substituted phenyl Grignard reagents; the arylmetal reagent is an aryl magnesium halide; and the palladium catalyst comprises a phosphine ligand.

10. The process of claim 1 wherein the vinylaromatic compound is a 1-aryl-3,4-dihydronaphthalene compound and the vinylphosphate is a 3,4-dihydronaphthalene-1-yl phosphate compound.

11. The process of claim 10 wherein the arylmetal reagent is an arylmagnesium halide.

12. The process of claim 10 wherein the palladium catalyst comprises a phosphine ligand.

13. The process of claim 10 wherein the 3,4-dihydronaphthalene-1-yl phosphate compound is prepared by reacting a 1-tetralone compound with a sterically hindered Grignard reagent and a halophosphate diester.

14. A process for the preparation of a vinylphosphate comprising reacting an enolizable ketone with a sterically hindered Grignard reagent and a halophosphate diester.

15. The process of claim 14 wherein the steric hindrance of the sterically hindered Grignard reagent is sufficient to provide at least a 75% yield of the vinylphosphate.

16. The process of claim 14 wherein the sterically hindered Grignard reagent is selected from secondary alkyl Grignard reagents, tertiary alkyl Grignard reagents and ortho-alkyl substituted phenyl Grignard reagents.

17. A process for the preparation of a 1-(4-alkoxyphenyl)-6-methoxy-3,4-dihydronaphthalene compound comprising the steps:

(a) reacting 6-methoxy-1-tetralone with a mesityl Grignard reagent and a halophosphate diester to produce a 6-methoxy-3,4-dihydronaphth-1-yl phosphate compound; and (b) reacting the 6-methoxy-3,4-dihydronaphth-1-yl phosphate compound with a 4-alkoxyphenylnagnesium halide in the presence of a palladium catalyst comprising a phosphine ligand.

18. The process of claim 17 wherein the 4-alkoxy group is a 4-[2-(dialkyl-amino)ethoxy] group.

19. The process of claim 18 wherein the 4-(2-dialkylamino)ethoxy group is a 4-[2-(pyrrolidin-N-yl)ethoxy] group.

20. The process of claim 17 wherein the mesityl Grignard reagent is mesitylmagnesium bromide.

21. The process of claim 17 wherein the halophosphate diester is selected from diphenyl chlorophosphate and diethyl chlorophosphate.

* * * * *